United States Patent [19]

Lockhoff et al.

[11] Patent Number: 4,686,208
[45] Date of Patent: Aug. 11, 1987

[54] PHOSPHORYLATED GLYCOSYL-AMIDES, -UREAS, -CARBAMATES AND -THIOCARBAMATES AND METHOD OF USE

[75] Inventors: Oswald Lockhoff, Cologne; Bernd-Wieland Krüger, Wuppertal; Peter Stadler; Arnold Paessens, both of Haan; Gert Streissle, Wuppertal, all of Fed. Rep. of Germany; Peter Taylor, West Haven, Calif.; Hans-Joachim Zeiler, Velbert; Karl-Georg Metzger, Wuppertal, both of Fed. Rep. of Germany

[73] Assignee: Bayer Aktiengesellschaft, Leverkusen, Fed. Rep. of Germany

[21] Appl. No.: 673,811

[22] Filed: Nov. 21, 1984

[30] Foreign Application Priority Data

Nov. 23, 1983 [DE] Fed. Rep. of Germany ....... 3342308
Feb. 2, 1984 [DE] Fed. Rep. of Germany ....... 3403495

[51] Int. Cl.$^4$ .......................... A61K 31/70; C07H 5/06
[52] U.S. Cl. ...................................... 514/42; 536/18.2; 536/22; 536/53; 536/117
[58] Field of Search ............... 536/18.2, 22, 53, 117; 514/42

[56] References Cited

U.S. PATENT DOCUMENTS 4,228,274 10/1980 Ponpipom et al. ................. 536/22
4,574,122 3/1986 Kruger et al. ...................... 536/53

FOREIGN PATENT DOCUMENTS 0147777 7/1985 European Pat. Off. ............. 514/42
3403495 5/1985 Fed. Rep. of Germany ....... 536/22

OTHER PUBLICATIONS

Lockhoff et al., "Chem. Abst.", vol. 104, 1986, p. 34303(g).

*Primary Examiner*—Johnnie R. Brown
*Attorney, Agent, or Firm*—Sprung Horn Kramer & Woods

[57] ABSTRACT

Compounds of the formula

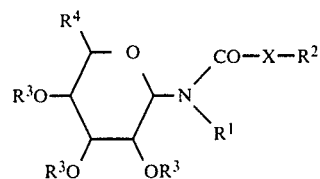

in which
  $R^1$ represents an optionally substituted, straight-chain or branched, saturated, monounsaturated or polyunsaturated alkyl radical, an optionally substituted, saturated or one- or polyunsaturated cycloalkyl radical or an optionally substituted aryl radical or aralkyl radical,
  X represents $CH_2$, O, S, NH or N-alkyl with up to 20 C atoms,
  $R^2$ has the meaning of $R^1$, and can represent hydrogen if X denotes $CH_2$, the radicals $R^3$ independently of one another represent hydrogen, an acyl radical or alkyl radical with in each case up to 20 C atoms, a silyl radical and/or a phosphoric acid or phosphoric acid ester radical and
  $R^4$ denotes hydrogen, methyl or $-CH_2-OR^3$, with the proviso that one of the radicals $R^3$ always represents a phosphoric acid or phosphoric acid ester radical, which stimulate a patient's immune system and are thereby effective in combating viral disease and bacterial infection.

15 Claims, No Drawings

PHOSPHORYLATED GLYCOSYL-AMIDES, -UREAS, -CARBAMATES AND -THIOCARBAMATES AND METHOD OF USE

The invention relates to new monophosphorylated N-glycosylamides, N-glycosylureas, N-glycosylcarbamates and N-glycosylthiocarbamates, processes for their preparation and their use as medicaments.

The new compounds correspond to the general formula I

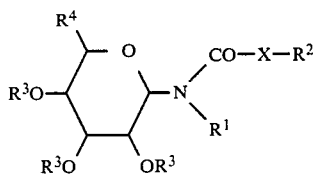

In this formula, $R^1$ denotes an optionally substituted straightchain or branched, saturated or monounsaturated or polyunsaturated alkyl radical, an optionally substituted, saturated or one- or polyunsaturated cycloalkyl radical or an optionally substituted aryl radical or aralkyl radical, X denotes $CH_2$, O, S, NH or N-alkyl, it being possible for this alkyl radical to contain up to 20, preferably 1-10, carbon atoms, $R^2$ has the meaning of $R^1$ and can additionally represent hydrogen if X represents $CH_2$, the radicals $R^3$ independently of one another denote hydrogen, an acyl radical with 1 to 20, preferably 1-10, carbon atoms, an alkyl radical with 1 to 20, preferably 1-10, carbon atoms, a silyl radical and/or a phosphoric acid or phosphoric acid ester radical and $R^4$ denotes hydrogen, methyl or $-CH_2-O-R^3$, with the proviso that one of the radicals $R^3$ always represents a phosphoric acid or phosphoric acid ester radical.

An alkyl radical $R^1$ has up to 40 C, preferably up to 20, C atoms, and very particularly preferably 10-20 C atoms.

Examples of saturated alkyl radicals $R^1$ are methyl, ethyl, n-propyl, i-propyl, n-butyl, i-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, eicosyl, docosyl, tetracosyl, triacontyl, ethylpentyl, methyldecyl, i-propyldecyl, methyltridecyl, pentylhexadecyl, 1-dodecylhexadecyl, 2-dodecylhexadecyl, 3-dodecylhexadecyl, 1-hexadecyloctadecyl, 2-hexadecyloctadecyl, 3-hexadecyloctadecyl, 4-hexadecyloctadecyl, 1-octadecyleicosyl and 2-octadecyleicosyl.

Examples of unsaturated alkyl radicals $R^1$ are ethenyl, prop-1-enyl, prop-2-enyl, i-butenyl, but-1-enyl, but-2-enyl, pent-1-enyl, pent-2-enyl, pent-3-enyl, pent-4-enyl, hex-1-enyl, hex-2-enyl, hex-3-enyl, hex-4-enyl, hex-5-enyl, dec-1-enyl, dec-5-enyl, dec-9-enyl, heptadec8-enyl, buta-1,3-dienyl, penta-1,3-dienyl, penta-1,4-dienyl, heptadecane-8,11-dienyl and heptadecane-8,11,14-trienyl.

In general, of the unsaturated radicals, the longer-chain radicals are preferred, in particular the monounsaturated or diunsaturated alkenyls with 10-20 carbon atoms.

The unsaturated hydrocarbon radicals can be in the form of pure cis- or trans-isomers or as isomer mixtures here.

A cycloalkyl radical $R^1$ is preferably a radical with 3-7 C atoms.

Examples of cycloalkyl radicals are cyclopropyl, cyclobutyl, cyclopentyl, cyclohexyl, cycloheptyl, cyclohexylcyclohexyl and cyclopentylcycloheptyl.

Examples of unsaturated cyclic radicals $R^1$ are cyclopentenyl, cyclohexenyl and cycloheptenyl. Preferred substituents for cycloalkyl radicals are alkyl radicals with up to 8 C atoms.

Examples of these which may be mentioned are: methylcyclopentyl, ethylcyclopentyl, n-propylcyclopentyl, i-propylcyclopentyl, butylcyclopentyl, octylcyclopentyl, methylcyclohexyl, ethylcyclohexyl, propylcyclohexyl, butylcyclohexyl, hexylcyclohexyl, decylcyclohexyl, cyclopentylmethyl, cyclopentylethyl, cyclopentylpropyl, cyclopentylbutyl, cyclopentylpentyl, cyclopentylhexyl, cyclopentyloctyl, cyclopentyldecyl, cyclohexylmethyl, cyclohexylethyl, cyclohexylpropyl, cyclohexylbutyl, cyclohexyl, cyclohexyldecyl, cyclopentylcyclohexylethyl, cyclohexylcyclopentylethyl and cyclohexylcyclohexylethyl.

The substituents can in each case be arranged in the cis- or trans-position.

An aralkyl radical $R^1$ can take many forms. Thus, on the one hand, the aryl radical, which preferably consists of 6 or 10 carbon atoms, can be present as a substituent on the alkyl chain, but it can also be inserted into the alkyl chain. Preferably 1-3 aryl radicals can be present when bonded in these ways. The aryl radicals can additionally be substituted, and, in particular, preferably by 1 or 2 groups from the series comprising nitro, lower alkyl ($C_1-C_4$) and $C_1-C_4$-alkoxy and they can carry up to 5 halogen atoms, preferably fluorine and chlorine.

An aryl radical $R^1$ is preferably a $C_6$-, $C_{10}$- or $C_{12}$-aromatic radical. These radicals can optionally be substituted, preferably by $C_1-C_4$-alkyl, $C_1-C_4$alkoxy or nitro, in each case preferably by 1-2 substituents, or by 1-5 halogen atoms, preferably fluorine or chlorine.

Examples of aryl and aralkyl radicals $R^1$ are phenyl, diphenyl, p-nitrophenyl, ethylphenyl, para-methoxyphenyl, 2,4-dichlorophenyl, benzyl, para-methoxybenzyl, phenylethyl, phenylhexyl, tolylheptyl, 2-phenyltetradecyl and 14-phenyltetradecyl.

In the radicals $R^1$, especially where these denote alkyl and alkenyl, it is also possible for individual methylene groups or methine groups to be replaced by oxygen, sulphur or nitrogen atoms. If the alkyl chain is interrupted by N, this nitrogen atom can carry either H or an alkyl radical with up to 20, preferably up to 6, carbon atoms or a CO-alkyl radical with up to 20, preferably up to 6, C atoms.

In general, up to 5, preferably one to three, methylene or methine groups can be replaced in this manner.

The radicals $R^1$ can be substituted, preferably by $C_6$-, $C_{10}$- or $C_{12}$-aryl, halogen, preferably F, Cl or Br, amino, $C_1-C_6$-alkylamino, di-$C_1-C_6$-alkylamino, OH, $C_1-C_6$-alkoxy, O-CO-R' or NH-COR', R' in each case representing $C_1-C_6$-alkyl. If $R^1$ is substituted, 1 or 2 identical or different substituents are preferably present.

Examples in which the radicals $R^1$ in formula I represent hydrocarbon radicals interrupted by oxygen-, sulphur- and/or nitrogen atoms of the said atoms contained therein are substituted are methoxyethyl, methoxyethoxyethyl, dimethylaminoethoxyethyl, dibutylaminohexyl, mercaptoethyl, oxobutyl, aminodecyl, N-methylaminodecyl, chloroethyl, fluoromethyl, 2-hydroxy-tetradecyl, 7-phenyloctadecyl, 16-phenylhexadecyl, 2-bromopropyl, 8-bromododecyl, 16-chlorohexadecyl, 2-aminotetradecyl, 16-aminohexadecyl, 4-(butylamino)-hexadecyl, 8-(dimethylamino)octadecyl, 8-hydroxyoctadecyl, 4-methoxydodecyl, 5-(butylcarbonyloxy)tridecyl, 2-(tridecylcarbonyloxy)tetradecyl, 2-(tridecylcarbonylamido)-tetradecyl, 2-hydroxyoctadec-8-en-1-yl, 2-aminooctadec-8-en-1-yl and tridecylcarbonyloxyoctadec-8-en-1-yl.

In the radical $R^3$, the acyl radical and the alkyl radical can in turn be substituted. 1–2 substituents from the group comprising halogen (F, Cl and Br, preferably Cl); aryl, preferably phenyl or phenyl which is substituted by 1–2 halogen atoms or $C_1$-$C_4$-alkoxy radicals; and $C_1$-$C_4$alkoxy, are particularly suitable here.

Examples of $R^3$ from the acyl series are acetyl, propionyl, butyryl, pivaloyl, benzoyl, p-methoxybenzoyl, 2,4-dichlorobenzoyl, caproyl, myristoyl and stearoyl.

Examples of $R^3$ from the alkyl series are methyl, ethyl, propyl, i-propyl, heptyl, decyl, octadecyl, allyl, 1-propenyl, benzyl, p-methoxybenzyl, ethylidene, isopropylidene, isobutylidene, benzylidene, p-methoxybenzylidene and 1-methoxyethylidene.

Examples of $R^3$ from the silyl ether group are trimethylsilyl and diethylpropylsilyl.

A phosphoric acid radical $R^3$ is to be understood as meaning —$PO(OH)_2$, and a phosphoric acid ester radical $R^3$ is to be understood as meaning the groups

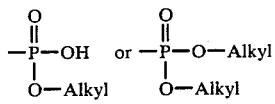

wherein
"alkyl" in each case independently represents a straight-chain or branched alkyl radical with 1–20, preferably with 1–5, C atoms.

As can be seen in formula I, the compounds according to the invention are based on a sugar molecule, preferably pentoses and hexoses.

Examples of such sugars are ribose, arabinose, xylose, lyxose, allose, altrose, glucose, mannose, gulose, idose, galactose and talose, both in the D-series and in the L-series.

The compounds according to formula I always contain, as one of the radicals $R^3$ or in the radical $R^4$, a phosphoric acid group or a phosphorous ester group, which is bonded to a hydroxyl group of the sugar part in an ester-like manner.

In the case where pentoses are the sugar constituents of the compounds according to formula I, one of the secondary hydroxyl groups belonging to the sugar ring is thus phosphorylated. In the case where hexoses form the sugar constituents of the compounds according to formula I, either the secondary hydroxyl group belonging to the ring or the hydroxyl group of the exocyclic hydroxymethyl group is phosphorylated.

The non-phosphorylated hydroxyl groups are either free, that is to say non-blocked, or blocked by esters, ethers and/or silyl radicals.

The compounds of the formula I contain several chiral C atoms and are in the form of optically pure diastereomers or of diastereomer mixtures.

The invention also relates to processes for the preparation of the compounds according to formula I. In these processes, the sugars described by formula I are reacted, either in the free, that is to say non-protected, form or in the form of protected and optionally partially phosphorylated and/or optionally activated derivatives, first with an amino compound $R^1$—$NH_2$, either in the free form or in the form of a suitable acid addition salt, with the above meaning of $R^1$. The glycosylamines obtained in this manner, of the formula II

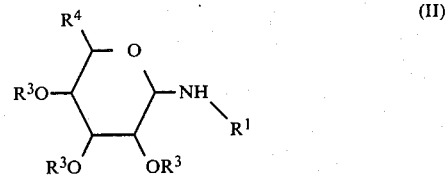

with the abovementioned meanings of $R^1$, $R^3$ and $R^4$ are then reacted with a carboxylic acid or carbonic acid derivative which is activated—as is customary in acylation reactions—and optionally protected on the functional groups, to give the glycosylamide, glycosylurea, glycosylcarbamate or glycosylthiocarbamate. If partially phosphorylated sugars have not been used from the beginning, the phosphate group is introduced in the third reaction step, which can, of course, consist of a number of reactions. Any protective groups present in the reaction products thus obtained are split off and the compounds of the formula I are obtained in this manner, and can, if necessary, be purified by chromatography, recrystallization, extraction or the like.

In a preferred embodiment of the process according to the invention, a non-blocked sugar of the aldopentose or aldohexose series is reacted with an amine $R^1$—$NH_2$ in a manner which is known per se in a first process step, a glycosylamine of the formula II being formed, with splitting off of water. In this case, $R^3$ represents hydrogen and $R^4$ represents either hydrogen, methyl or hydroxymethyl.

Amines $R^1$—$NH_2$ which are liquid at room temperature can be reacted directly with the sugar, that is to say without a solvent. In this case, the reaction is carried out at a temperature between 0° C. and 100° C., preferably 25° C. and 70° C. Suitable catalysts are mineral acids, such as, for example, hydrochloric acid or sulphuric acid, or shortchain carboxylic acids, such as acetic acid or propionic acid, which are used in amounts of 0.001 to 0.05 equivalents.

It is in all cases possible, and for amines $R^1$—$NH_2$ which are solid at room temperature also preferable, to carry out the preparation of the glycosylamines in the presence of a solvent. The reaction is then preferably carried out in the presence of a diluent which is inert under the reaction conditions and is preferably such that at least either the reactants or the reaction mixture dissolve therein.

Possible diluents are alcohols, such as methanol, ethanol, 1-propanol and 2-propanol, ethers, such as tetrahydrofuran and dioxane, and dimethylformamide, the addition of water, if appropriate, being preferred.

The reaction temperatures are between $-10°$ C. and 120° C., preferably between 30° C. and 70° C., when solvents are used in the preparation of the glycosylamines.

The diluent in question can be added before or during the reaction, as desired. In the case of longchain amines $R^1$—$NH_2$, addition before the reaction is to be preferred.

The glycosylamines prepared as described above crystallize out either directly or after cooling, and can be crystallized out or made to crystallize by addition of suitable auxiliaries, preferably auxiliaries of low polarity, such as acetone, diethyl ether, cyclohexane, ethyl acetate or petroleum ether, if appropriate with cooling. Any excess amine $R^1$—$NH_2$ present can be removed by washing or recrystallizing the product in a manner which is known per se. The glycosylamines of the formula II obtained in this manner are acylated selectively on the nitrogen atom with carboxylic apid derivatives or carbonic acid derivatives in the second reaction step to give glycosylamides, glycosylcarbamates, glycosylthiocarbamates or glycosylureas.

In the case where X in formula I represents a methylene group, the corresponding glycosylamines of the formula II are reacted with 1 to 10 equivalents of a carboxylic acid derivative of the formula $R^2$—$CH_2$—CO—Y, in which $R^2$ has the abovementioned meaning and Y denotes for halogen or a leaving group customary in amidation reactions, preferably an activating ester radical, such as, for example, para-nitrophenyl, or a group O—CO—$R^2$, with the above meaning for R2, or a group O—CO—$R^2$, with the above meaning of $R^2$. This reaction is carried out in organic or aqueous-organic solvents at temperatures between 0° C. and 50° C., if appropriate in the presence of a base.

In the case where X in formula I represents an oxygen atom, a glycosylamine of the formula II is reacted with 1 to 5 equivalents of a halogeno-carbonic acid ester Y—CO—O—$R^2$, wherein Y represents halogen, preferably chlorine, and $R^2$ has the meaning described above. This reaction is carried out in organic solvents at temperatures between $-20°$ C. and 50° C., if appropriate in the presence of a base.

In the case where X in formula I represents a sulphur atom, a glycosylamine of the formula II is reacted with a thiocarbonic acid halide S-ester $R^2$—S—CO—Y, wherein Y represents halogen, preferably chlorine, and $R^2$ has the above meaning. The reaction is carried out in organic solvents, if appropriate in the presence of a suitable catalyst and/or a base, and the reaction temperatures are between 0° C. and 70° C.

In the case where X in formula I denotes an NH group, a glycosylamine of the formula II is reacted with 1 to 5 equivalents of an isocyanate $R^2$—NCO with the above-mentioned meaning of $R^2$. The reaction is preferably carried out in organic solvents, if appropriate in the presence of a catalyst, and the reaction temperatures are between $-20°$ C. and 50° C.

In the case where X in formula I denotes an NH group or an N-alkyl group, it is also possible to react a carbamate, which is obtained by reaction of an amine according to formula II with a preferably aromatic halogenoformic acid ester, with 1 to 10 equivalents of a primary amine $R^2$—$NH_2$ or of a secondary amine $R^2$—NH—alkyl, with the meanings for $R^2$ described above. The reaction is preferably carried out at 20° C. to 80° C. in organic solvents, if appropriate in the presence of a catalyst.

The carboxylic acid derivatives and carbonic acid derivatives are preferably reacted with the glycosylamines in the presence of a diluent in which the reactants dissolve completely or even only partly.

Organic or inorganic solvents are possible, preferably those which as far as possible reduoe prevent side reactions under the reaction conditions. The reaction can be carried out either in organic solvents, such as ethers, for example tetrahydrofuran or dioxane, or alcohols, such as, for example, ethanol or propanol, or ketones, such as acetone or methyl ethyl ketone, or in dimethylformamide or ethyl acetate or pyridine, or in mixtures of these solvents with one another and/or with water. It is in general preferable to use anhydrous solvents.

The reactions with the carboxylic acid derivatives or the carbonic acid derivatives can be carried out in the presence of basic auxiliaries. It is possible to use all the basic compounds customary in organic synthesis, such as, for example, tertiary aliphatic or aromatic amines, such as triethylamine or pyridine, or alkali metal hydroxides or carbonates or alkaline earth metal hydroxides or carbonates, such as sodium hydroxide, sodium carbonate or calcium carbonate. The N-glycosylamides, -carbamates, -thiocarbamates or -ureas obtained in this manner are isolated by processes which are known per se in the form of crystalline or amorphous solids or as viscous syrups and, if necessary, are purified by crystallization, chromatography, extraction and the like.

In the case of compounds with protected hydroxyl groups in the glycosyl part, the protective groups can be split off in a manner which is known per se.

The phosphorylation for the preparation of the compounds of the formula I according to the invention can be carried out by any method which is suitable for synthesis of the P-O-C bond.

In those cases where one hydroxyl group is more reactive than the other hydroxyl groups in the sugar ring—this is, for example, the primary hydroxyl group or C atom 6 of the carbohydrate part—the phosphorylation can be carried out by conventional methods which are known for selective phosphorylation reactions, for example from nucleoside and carbohydrate chemistry. Such a method generally comprises reaction of an N-alkyl-N-(aldohexopyranosyl)-carboxamide, -urea, -carbamate or -thiocarbamate with a phosphorylating reagent in an organic solvent.

A number of solvents can be used as the suitable solvent, for example hydrocarbons, such as hexane, cyclohexane or toluene, halogenohydrocarbons, such as methylene chloride, chlorohexane or chlorobenzene, phenols, such as phenol or cresol, organic acid esters, such as ethyl acetate or methyl benzoate, nitro compounds, such as nitromethane, nitroethane or nitrobenzene, nitriles, such as acetonitrile or malononitrile, ethers, such as diethyl ether, tetrahydrofuran, dioxane or ethylene glycol dimethyl ether, or trialkyl phosphates, such as trimethyl phosphate or triethyl phosphate.

These solvents can be used either by themselves or as a mixture with one another, or as a mixture with an organic base, such as pyridine, triethylamine or picoline, or with a salt of an organic base and an inorganic or organic acid, such as pyridine hydrochloride or pyridinium para-toluenesulphonate.

Suitable phosphorylating reagents are phosphorus halides, such as phosphorus trichloride, phosphorus oxychloride, phenyl phosphorus dichloridate, diphenyl phosphochloridate, dibenzyl phosphochloridate, monoalkyl phosphorus dichloridate, dialkyl phosphochloridate or partially hydrolyzed phosphorus oxychlorides. An example of a particularly suitable combination of reagent and solvent is phosphorus oxychloride and trialkyl phosphate or dibenzyl phosphochloridate and methylene chloride/toluene and pyridine.

The reaction temperature is between −20° C. and +50° C., preferably between 0° C. and room temperature, and the reaction time is between a few hours and a few days.

In the cases where selective phosphorylation of a hydroxyl group cannot be carried out because either a less reactive secondary hydroxyl group in the sugar residue is to be phosphorylated in the presence of a more reactive primary hydroxyl group, or a secondary hydroxyl group is to be phosphorylated selectively in the presence of other secondary hydroxyl groups, the actual phosphorylation is to be preceded by a number of protective group operations, in which the hydroxyl group to be phosphorylated is selectively present in the free, that is to say unsubstituted, form at the end of the blocking reactions. The hydroxyl groups which are not to be phosphorylated must therefore be blocked before the phosphorylation.

Suitable protective groups for sugar derivatives are described in the relevant literature (for example C. B. REESE, in: Protecting Groups in Org. Chem., 1973, pages 95–143; Plenum Press). All the protective groups and combinations thereof used in sugar chemistry can be used.

Examples of suitable protective groups are esters, such as acetyl, benzoyl, pivaloyl and p-methoxybenzoyl, ethers, such as benzyl, p-methoxybenzyl, allyl and prop-1-enyl, alkylidene compounds, such as ethylidene, isopropylidene and benzylidene, ortho-esters, such as 1-methoxyethylidene, 1-ethoxyethylidene, silyl ethers, such as trimethylsilyl and t-butyldimethylsilyl, and organometallic compounds, such as boric acid esters or tin ethers or tin ketals, such as tributyl-stannyl or dibutyl-stannylidene.

The carbohydrate derivatives blocked by these protective groups are then phosphorylated, in a suitable solvent, on the hydroxyl group which is still free. Suitable solvents and suitable processes for the phosphorylation are mentioned above.

For the preparation of the free compounds according to formula I, any protective groups present are then split off by the customary methods.

The monophosphorylated glycosyl-amides, -carbamates, -thiocarbamates or -ureas according to formula I are isolated and purified by conventional methods. For example, the isolation and purification can be carried out by a selection or combination of the current purification methods, such as adsorption chromatography on silica gel or ion exchanger resins, extraction or crystallization.

The invention also includes salts of the compounds of the formula I.

These salts are, above all, non-toxic salts which can usually be employed pharmaceutically, such as, for example, alkali metal, alkaline earth metal or ammonium salts.

The compounds of the present invention exhibit useful pharmacological properties, in particular a pronounced antiviral and immunostimulating action.

Generally it can be said, that the compounds of the invention, if orally or parenterally administered, are administered in an amount of 1–50 mq/kq, if administered topically they are usually applied in a solution in a suitable solvent, preferably DMSO or DMSO-water mixtures, or in ointments having a concentration of 0,1–20%, preferably 1–10% of the compounds of the invention.

It has been found that the compounds of the invention inhibit virus reproduction and significantly increase the interfering titres caused by a virus infection or by interferon induction.

These actions can be demonstrated with the aid of the experimental design described below.

Antiviral action

EXAMPLE A

Animal experiment/cutaneous test on guinea pigs

The test was carried out in accordance with the method developed by Hubler et al. (J. Invest. Dermatol. 62, 92–95, (1974)). Guinea pigs weighing 500 to 600 g were shaved on the ventral side and anaesthetized with Nembutal (15 mg/kg intraperitoneally). Previously marked areas of skin were infected with a multiple scarificator (vaccination gun). A medium of rabbit kidney cells which had been infected with herpes simplex virus type I was used as the virus material. The treatment can be carried out locally, parenterally, orally, intraperitoneally or intravenously. Infected animals which had not been treated or were treated with placebo served as controls.

If administered topically, a 5% solution of the compounds of the invention in 90% DMSO—10% water is preferred.

In this test the compounds were administered three times a day for a period of three days, but it is also possible to have them administered less frequently or more frequently and for a shorter or longer period of time. Evaluation was according to the number and size of the herpes blisters. Compounds of the present invention—as shown in Table 1—reduced the number and size of the virus-induced induced blisters.

TABLE 1

Antiviral action of the phosphorylated glucosyl derivative according to Example 6 on virus-infected skin of guinea pigs (topical application)

| Guinea pig | No. | Outbreak of infection | | | | Healing | | |
|---|---|---|---|---|---|---|---|---|
| | | Day | | | | | | |
| | | 2 | 3 | 4 | 5 | 6 | 7 | 8 |
| Untreated | 1228 | 20 | 30 | 100 | 95 | 60 | 20 | 10–20 |
| Control | 1229 | 20 | 70 | 90 | 85 | 55 | 20 | 10 |
| | 1230 | 10–20 | 70 | 100 | 95–100 | 50 | 20 | 10 |
| | 1231 | 15 | 30 | 80 | 70 | 60 | 20 | 10 |
| Placebo Control | 1232 | 20 | 30 | 100 | 100 | 60 | 20 | 10 |
| 90% DMSO | 1233 | 10 | 20 | 50 | 50 | 60 | 20 | 10 |
| 10% H$_2$O (v/v) | 1234 | 80 | 70–80 | 100 | 89–90 | 50 | 20 | 10 |
| +5% of compound | 1241 | 10 | 20 | 5–10 | 20 | 30 | 15 | 10 |
| in DMSO-H$_2$O, 9:1 | 1242 | 15 | 10 | 10 | 20 | 25 | 10 | 10 |
| (v/v) according to | 1243 | 20 | 60–70 | 10 | 30 | 35 | 15 | 10 |

TABLE 1-continued

Antiviral action of the phosphorylated glucosyl derivative according to Example 6 on virus-infected skin of guinea pigs (topical application)

| Guinea pig | No. | Outbreak of infection | | | | Healing | | |
|---|---|---|---|---|---|---|---|---|
| | | Day | | | | | | |
| | | 2 | 3 | 4 | 5 | 6 | 7 | 8 |
| Example 6 | | | | | | | | |

100% = large lesions with partly confluent blisters
50% = lesions with medium-size blisters
20% = a few small lesions, without blistering

Interferon-stimulating action

EXAMPLE B

The test was carried out in accordance with the method developed by Merigan et al. (Nature 268, 67 (1977). CFI mice (Winkelmann, Borcken) 6–8 weeks old were infected intraperitoneally with 0.1 ml of a solution of the virus of lymphocytic choriomeningitis (LCM). A homogenate of LCM infected mice brains was used as the virus material.

Infected animals which had not been treated or were treated with placebos served as controls.

The animals were treated prophylactically and therapeutically by the intraperitoneal route (day −1, 0, 1 and 2).

It is also possible to treat the animals therapeutically only.

The serum from the mice was tested for interferon activity after the times shown in Table 2. Before testing, the interferon-containing material were dialyzed at pH 2 in order to inactivate residual viruses.

The interferon level was determined by the method of Havell et al. (Antimicrob. Agents Chemother. 2, 476 (1972).

TABLE 2

Serum interferon titre (U/ml) after treatment of LCM-infected mice with the compound according to Example 6.

| | Day 1 | Day 2 | Day 3 |
|---|---|---|---|
| Control | 0 | 800 | 2,800 |
| 5 mg/kg of compound according to Example 6 | 0 | 5,600 | 4,000 |
| 25 mg/kg | 3,600 | 9,600 | 6,400 |

Compounds of the present invention—as shown in Table 2—are capable of increasing the interferon titre as a function of the dose (up to 12-fold stimulation).

The interferon-stimulating effect of the compounds mentioned depends on an additional stimulation (virus, interfon inducter), that is to say only when the new compounds are injected together with interferon inducers is the result an increase in the interferon level.

As already mentioned, the compounds of the formula (I) according to the invention have a powerful antiviral and immunostimulating action.

This action applies to all viruses which are interferon-sensitive.

Examples of acute infections which may be mentioned as fields of indication in human medicine are: viruses of the herpes group, influenza, rhinoviruses and entero-viruses.

For persistent infections: for example viruses of the herpes group and hepatitis B.

Examples of indications in veterinary medicine which may be mentioned are: infections with pseudorabies virus (cattle, pigs), rhinotracheitis virus (cattle) and rhinopneumonitis (horse), and Marek virus (chicken), Newcastle disease virus (chicken) and foot and mouth disease (cattle, pig).

The interferon-stimulating action of the new compounds is suitable for stimulation of the endogenous defenses, for example by influencing macrophages and "natural killer" cells.

It has furthermore been found that the compounds of the invention increase the antibody synthesis of the immune system in an antigen-specific manner, and moreover intensify the non-specific defenses endogenous in the host. These results have been obtained with the aid of the following experimental designs. Increase in the primary humoral immunity against sheep erythrocytes (SE) in vitro.

It is possible, experimentally, to initiate in vitro the development of a humoral immune response with heterologous red blood cells by primary immunization of mouse spleen cells in suspension cultures (R. I. Mishell and R. W. Dutton, J. Exp. Med. 126, 423 (1967)). For this purpose, Balb/c mouse spleen cells were cultured for 5 days in the presence of antigen (SE) and the test substance. The cells are harvested, washed and plated out in semisolid agar, together with the antigen and complement, and incubated at 37° C. for 2 hours (N. K. Jerne, A. A. Nordin and C. Henryl, "Cell bound Antibodies", editors Amos and Koprowski, Wistar Inst. Press, Philadelphia, USA, page 109 (1963)). The antigen-sensitisation of mouse lymphocytes in the primary culture results in the synthesis and release of antibodies (Ab). The specific antibodies which are released bind to the SE antigen and lyse these cells due to the presence of complement (plaque formation). The substances of the present invention are capable of increasing the number of antibody-forming cells as a function of the dose in the range from 1 to 100 $\mu$g/ml. Increase in the primary humoral immunity against the soluble antigen ovalbumin in vivo.

NMRI mice were immunized subcutaneously (s.c.) with a suboptimal antigen dose (1 $\mu$g/animal, day 0). With suboptimal antigen stimulation, only a small number of lymphocytes of the animals were stimulated to antibody synthesis. The additional treatment of the animals with compounds of the present invention is capable of significantly (p≦0.03) increasing the antibody titre in the serum of the animals following a single subcutaneous administration of 30 mg/kg. The antibody titre was detecmined by indirect haemagglutination on day 10. The effect of the treatment is expressed by the geometric mean of the $\log_2$ titre.

In contrast to other immunostimulants, for example bacterial immunostimulants, such as LPS from Gram-negative bacteria, the immunostimulating effect of the compounds according to the invention is antigen-dependent, that is to say the substances surprisingly cause induction of the antibody synthesis only in conjunction with an antigenic stimulation (in this case SE or ovalbumin). In contrast to the conventional immunostimulants (for example LPS), they have no mitogenic properties.

Tolerance

Although compounds of the type described already display their potentiating action in mice, for example, after a single intraperitoneal or peroral dose of 10 mg/kg, no toxic effects are observed even on administration of 100 mg/kg. The substances mentioned therefore are well tolerated.

The compounds according to the invention have the ability, on the one hand, to increase the immunogenicity of an antigen when mixed with the antigen and, on the other hand, to increase the immunological response of the treated organism when administered systemically. The substances mentioned are thereby capable of activating the lymphocytes responsible for antibody formation.

The new compounds can thus be used as adjuvants in mixtures with vaccines to improve the success of the vaccination and to increase the protection from infection by bacterial, viral or parasitic pathogens imparted by immunity.

When mixed as adjuvants with the most diverse antigens, the compounds described are furthermore suitable in the experimental and industrial preparation of antisera for therapy and diagnostics.

Moreover, without the simultaneous administration of antigens, the new compounds can also be used, in humans and animals, to promote defense reactions which are already proceeding at a subthreshold level. The compounds are accordingly particularly suitable for the stimulation of endogenous defenses, for example in cases of chronic and acute infections or in cases of selective (antigen-specific) immunological deficiencies, as well as in cases of congenital and also acquired general (that is to say not antigen-specific) immunological deficiency conditions, such as occur in old age, in the course of serious primary diseases and, in particular, after therapy with ionizing rays or with substances having an immunosuppressant action. The substances mentioned can thus preferably also be administered in combination with antiinfectious antibiotics, chemotherapeutics or other healing methods, in order to counteract immunological damage. Finally, the substances described are also suitable for general prophylaxis of infectious diseases in humans and animals.

The compounds according to the invention can be used by themselves as a prophylactic agent for combating existent infection or in combination with antibiotic therapy for increasing the therapeutic action of antibiotics and chemotherapeutics (for example penicillins, cephalosporins, aminoglycosides and the like) in infected humans and animals.

It has been found that infections in mice with pathogenic organisms which lead to death of the experimental animals within 24 to 28 hours can be treated therapeutically by prophylactic treatment—preferably intraperitoneally—with 1 to 20 mg/kg, for example, of the compounds according to the invention described in the examples. This applies to a large number of Gram-positive (for example Staphylococci) and Gram-negative (for example E.coli, Klebsiella, Proteus and Pseudomonas) pathogens.

This list is illustrative and is no way to be regarded as limiting. Thus, for example, 40 to 100% of mice which had been infected with the pathogenic strain Klebsiella 63 survived after treatment (for example 18 hours before infection) with 1 to 20 mg/kg of the compounds according to the invention, while only 0 to 30% of the untreated control animals survived. Detection of phenotypical changes from serum-resistant to serum-sensitive Gram-negative strains of bacteria.

Substances which modify the surface structures of Gram-negative bacteria are capable of modifying these bacteria so that they become more sensitive towards host defence mechanisms. It has been found that serum-resistant E.coli strains, which have been cultured in the presence of inhibitory concentrations of compounds according to the invention, are converted phenotypically into serum-sensitive forms. It has been possible to demonstrate this effect with the compound of Example 3 using a total of three different E.coli K1 strains (C10, C14, LP1674). Transition from serum-resistant to serum-sensitive bacteria took place.

EXAMPLES

1. N-Octadecyl-D-glucopyranosylamine 20 g of octadecylamine are dissolved in 120 ml of ethanol and the solution is warmed to 70° C. 11 g of anhydrous D-glucose are added. After a clear solution has formed, stirring is continued at 70° C. for a further 15 minutes. The solution is cooled to 10° C. and left to stand for 15 minutes. The crystal sludge formed is filtered off with suction, washed twice with ethanol and dried in vacuo.

Elemental analysis:
Calculated: C 66.8%; H 11.4; N 3.2%;
Found: C 67.4%; H 11.8; N 3.7%.

2. N-Glucopyranosyl-N-octadecyl-dodecanoic acid amide 10 g of the compound from Example 1 are suspended in 80 ml of tetrahydrofuran, and, after addition of 10 g of sodium carbonate, 10 g of dodecanoic acid chloride in 10 ml of tetrahydrofuran are added dropwise. When the reaction has ended (check by thin layer chromatography on silica gel 60 in toluene/isopropanol 6:1), the solid is filtered off, the filtrate is evaporated to a syrup in vacuo and the crude product is purified by column chromatography on silica gel 60 with the eluting agent toluene/isopropanol 10:1.

$[\alpha]_D^{20} = 8°$ (c=1.0 in dioxane).

3. N-(Glucopyranosyl-6-phosphate)-N-octadecyl dodecanoic acid amide 6.1 g of the compound from Example 2 are dissolved in 60 ml of methylene chloride. 6 g of dibenzyl phosphochloridate, dissolved in 10 ml of toluene, and 3.1 ml of pyridine are added to the solution. The batch is stirred overnight. It is then filtered, the filtrate is evaporated to a syrup in vacuo and the syrup is separated by column chromatography (eluting agent toluene/ethanol 10:1). The resulting main product (6 g) is dissolved in 100 ml of tetrahydrofuran and 10 ml of glacial acetic acid and hydrogenated in the presence of 2 g of palladium-on-charcoal (5% strength). When the uptake of hydrogen has ended, the catalyst is filtered off, the filtrate is evaporated to a syrup in vacuo and the syrup is co-evaporated several times with toluene.

$[\alpha]_D^{20} = 1.2°$ (c=1.0 in dimethylformamide)
Ammonium Salt:
$[\alpha]_D^{20} = 8°$ (c=0,065 in water)

4. N-Dodecyl-D-galactopyranosylamine

Preparation according to Example 1, from D-galactose and dodecylamine.
Elemental analysis:
Calculated: C 62.2%; H 10.7%; N 4.0%;
Found: C 62.5%; H 10.2%; N 4.4%.

5. N-Galactopyranosyl-N-dodecyl-octadecanoic acid amide

Preparation according to Example 2 from 10 g of the compound according to Example 4 and 16 g of stearoyl chloride.
$[\alpha]_D^{20} = 4.4°$ (c=1.0 in methylene chloride)
Rf value=0.23 in toluene/n-propanol 4:1

6. N-(D-Galactopyranosyl-6-phosphate)-N-dodecyl-octadecanoic acid amide

Preparation according to Example 3 from 6 g of the compound from Example 5, 7.5 g of dibenzyl phosphochloridate and 3.9 ml of pyridine and subsequent hydrogenation.
$[\alpha]_D^{20} = 11.5°$ (c=0.82 in dimethylformamide)
Disodium Salt:
$[\alpha]_D^{20} = 9°$ (c=0. 16 in water)

7. N-(D-Lyxopyranosyl)-N-dodecyl-dodecanoic acid amide 10 g of D-lyxose are dissolved in 120 ml of isopropanol and 60 ml of water and the solution is warmed to 70° C. 18 g of dodecylamine are added. After a clear solution has formed, the temperature is maintained for a further 15 minutes. The mixture is cooled to room temperature and evaporated in vacuo. 10 g of the resulting syrup are dissolved in 100 ml of tetrahydrofuran and 10 ml of methanol, and 10 g of sodium carbonate are added. 5.5 g of dodecanoic acid chloride, dissolved in 20 ml of tetrahydrofuran, are added dropwise at 0° C. When the reaction has ended, the mixture is worked up, and the product purified, as described in Example 2.
$[\alpha]_D^{20} = 5.3°$ (c=1.1 in tetrahydrofuran)
Elemental analysis:
Calculated: C 69.7%; H 11.5%; N 2.8%;
Found: C 69.6%; H 11.7%; N 2.7%.

8. N-(D-Lyxopyranosyl-4-phosphate)-N-dodecyl-dodecanoico acid amide 5 g of the compound from Example 7 are dissolved in 30 ml of tetrahydrofuran. 1 ml of 2,2-dimethoxypropane and 10 mg of para-toluenesulphonic acid are added and the mixture is warmed to 70° C. for 30 minutes. After cooling to room temperature, the mixture is neutralized with ion exchanger MP 500 (OH form) and evaporated several times with toluene in vacuo. The resulting syrup is dissolved in 50 ml of methylene chloride, and 6 g of dibenzyl phosphochloridate and 3.1 ml of pyridine are added and the mixture is stirred overnight. The solid formed is filtered off and the filtrate is concentrated to a syrup. The syrup is purified by column chromatography (eluting agent toluene/acetone 10:1). The resulting main product is dissolved in 30 ml of methylene chloride, and 2 ml of trifluoroacetic acid/water (99:1) are added at 0° C. After 10 minutes, the mixture is diluted with 30 ml of toluene and concentrated in vacuo. The residue is taken up in toluene and concentrated in vacuo three times. The resulting syrup is dissolved in 80 ml of tetrahydrofuran and 10 ml of glacial acetic acid and hydrogenated in the presence of 2 g of palladium-on-charcoal (5% strength). When the uptake of hydrogen has ended, the catalyst is filtered off, the filtrate is evaporated to a syrup in vacuo and the syrup is co-evaporated several times with toluene.
$[\alpha]_D^{20} = 2.7°$ (c=0.95 in tetrahydrofuran)

9. N-Octadecyl-N-(D-glucopyranosyl)-decylurethane 9 g of the compound from Example 1 are suspended in 160 ml of tetrahydrofuran and 40 ml of ethanol, and 9 g of sodium carbonate are added. 5 g of decyl chloroformate, dissolved in 40 ml of tetrahydrofuran, are added dropwise to this suspension in the course of 20 minutes. When the reaction has ended, the batch is filtered and the residue on the filter is rinsed with tetrahydrofuran. The filtrate is combined with the washing solutions and evaporated in vacuo. The resulting syrup is purified by chromatography (eluting agent methylene chloride/methanol, 20:1).
Rf value: 0.37 in $CH_2Cl_2/CH_3OH$ 10:1
Elemental analysis
Calculated: C 68.3%; H 11.3%; N 2.3%;
Found: C 68.4%; H 11.6%; N 2.4%.

10. N-Octadecyl-N-(D-glucopyranosyl-6-phosphate)-decylurethane

Preparation according to Example 3 from 6 g of the compound from Example 9, 7.5 g of dibenzyl phosphochloridate and 3.9 ml of pyridine, and subsequent hydrogenation.
$[\alpha]_D^{20} = 1.9°$ (c=0.75 in dimethylformamide)

11. N-Octadecyl-N-(D-glucopyranosyl)-N'-dodecylurea 9 g of the compound from Example 1 are suspended in 160 ml of tetrahydrofuran and 40 ml of ethanol. 4.3 g of dodecyl isocyanate, dissolved in 20 ml of tetrahydrofuran, are added dropwise to this suspension in the course of 20 minutes. When the reaction has ended, the mixture is evaporated in vacuo and the resulting syrup is purified by column chromatography (eluting agent methylene chloride/methanol, 15:1).
Rf value: 0.33 in $CH_2Cl_2/CH_3OH$ 10:1
$[\alpha]_D^{20} = 7.4°$ (c=1.04 in dioxane)

12. N-Octadecyl-N-(D-glucopyranosyl-6-phosphate)-N'decylurea

Preparation according to Example 3 from 6 g of the compound from Example 11, 7.5 g of dibenzyl phosphochloridate and 3.9 ml of pyridine, and subsequent hydrogenation.
$[\alpha]_D^{20} = 1.0°$ (c=2.10 in dimethylformamide)

13. N-Octadecyl-N-(D-glucopyranosyl-4-Phosphate)-dodecanoic acid amide 10 g of the compound from Example 2 are dissolved in 100 ml of tetrahydrofuran, 3.5 g of benzaldehyde dimethyl acetal and 10 mg of para-toluenesulphonic acid are added and the mixture is warmed at 70° C. for 1 hour. After cooling to room temperature, the mixture is neutralized with ion exchanger MP 500 (OH form) and concentrated under a high vacuum. The resulting syrup is taken in 100 ml of tetrahydrofuran and, after addition of 1.5 g of sodium hydride and 3.5 ml of benzyl bromide, the mixture is warmed at 40° C. for 1 hour. After cooling to room temperature, 20 ml of methanol are added and the mixture is subsequently stirred for 1 hour. 10 ml of water are carefully added to the batch and the mixture is concentrated under a high vacuum. The resulting syrup is taken up in 100 ml of methylene chloride, extracted twice with 20 ml of water each time, dried over magnesium sulphate and concentrated in vacuo and the residue is purified by column chromatography (eluting agent toluene/ethyl acetate 20:1).

The resulting syrup is dissolved in 30 ml of tetrahydrofuran and, after addition of 30 ml of glacial acetic acid/water 10:1, the mixture is warmed at 70° for 1 hour, cooled to room temperature and evaporated several times with toluene under a high vacuum. The resulting chromatographically uniform syrup (7.8 g) is dissolved in 100 ml of tetrahydrofuran, the solution is stirred with 400 mg of sodium hydride at 50° C. for 30 minutes and cooled to 0° C. and 1.8 g of benzyl bromide are added. After 3 hours, the mixture is warmed to room temperature and stirring is continued overnight. After addition of 5 ml of methanol, the mixture is subsequently stirred for 1 hour, water is then carefully added and the mixture is evaporated. The resulting residue is taken up in methylene chloride and water and the organic phase is extracted with water, dried and concentrated under a high vacuum. The residue is taken up in 10 ml of tetrahydrofuran and the solution is stirred overnight with 5.5 g of dibenzyl phosphochloridate and 2.8 ml of pyridine. The mixture is filtered, the filtrate is evaporated to a syrup in vacuo and the syrup is purified by column chromatography (eluting agent toluene-/ethyl acetate 15:1).

The resulting main product (3.9 g) is dissolved in 80 ml of tetrahydrofuran and 10 ml of glacial acetic acid and hydrogenated in the presence of 2 g of palladium-on-charcoal. When the uptake of hydrogen has ended, the catalyst is filtered off, the filtrate is evaporated to a syrup in vacuo and the syrup is coevaporated several times with toluene.

$[\alpha]_D^{20} = 1.9°$ (c=2.0 in dimethylformamide)

The following compounds were synthesized analogously to Examples 3 and 6 by reaction of the aldoses with alkylamines to give the aldosylamine, acylation thereof with fatty acid chlorides to give the aldosylamide and subsequent selective phosphorylation and hydrogenation:

14.
N-(Dodecyl)-N-(D-galactopyranosyl-6-phosphate)-hexadecanoic acid amide $[\alpha]_D^{20} = 12°$ (c=1.24 in dimethylformamide)

15.
N-(Dodecyl)-N-(D-galactopyranosyl-6-phosphate)-tetradecanoic acid amide

16.
N-(Tetradecyl)-N-(D-galactopyranosyl-6phosphate)-octadecanoic acid amide

17.
N-(Tetradecyl)-N-(D-galactopyranosyl-6-phosphate)-oleic acid amide

18.
N-(Tetradecyl)-N-(D-galactopyranosyl-6-phosphate)-hexadecanoic acid amide

19.
N-(Tetradecyl)-N-(D-galactopyranosyl-6-phosphate)-tetradecanoic acid amide

20.
N-(Hexadecyl)-N-(D-galactopyranosyl-6-phosphate)-dodecanoic acid amide

21.
N-(Octadecyl)-N-(D-galactopyranosyl-6-phosphate)-dodecanoic acid disodium salt: $[\alpha]_D^{20} = -0.1$ (c=0.43 in water)

22.
N-(Octadecyl)-N-(D-galactopyranosyl-6-phosphate)-tetradecanoic acid amide

23.
N-(Octadecyl)-N-(D-galactopyranosyl-6-phosphate)-octadecanoic acid amide

24.
N-(Octadecyl)-N-(D-glucopyranosyl-6-phosphate)-tetradecanoic acid amide $[\alpha]_D^{20} = -1°$ (c=0.35 in water)

25.
N-(Octadecyl)-N-(D-glucopyranosyl-6-phosphate)-octadecanoic acid amide disodium salt: $[\alpha]_D^{20} = +0.4°$ (c=0.1 in water)

26.
N-(Octadecyl)-N-(D-glucopyranosyl-6-phosphate)-oleic acid amide

27.
N-(Tetradecyl)-N-(D-glucopyranosyl-6-phosphate)-octadecanoic acid amide disodium salt: $[\alpha]_D^{20} = +6°$ (o=0.07 in water)

28.
N-(Octadecyl)-N-(D-mannopyranosyl-6-phosphate)-tetradecanoic acid amide disodium salt: $[\alpha]_D^{20} = +4°$ (c=0.25 in water)

29. N-(Octadecyl)-N-(D-mannopyranosyl-6-phosphate)-octadecanoic acid amide

30. N-(Tetradecyl)-N-(D-mannopyranosyl-6-phosphate)-octadecanoic acid amide

31. N-(Dodecyl)-N-(D-mannopyranosyl-6-phosphate)-octadecanoic acid amide

It will be understood that the specification and examples are illustrative but not limitative of the present invention and that other embodiments within the spirit and scope of the invention will suggest themselves to those skilled in the art.

We claim:

1. A compound of the formula

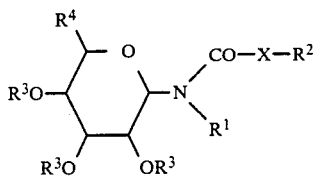

in which
R$^1$ represents an aliphatic hydrocarbon radical having up to 40 carbon atoms or an aliphatic hydrocarbon radical having up to 40 carbon atoms interrupted by at least one of oxygen, sulphur, NH, N-C$_1$—C$_{20}$-alkyl or N-CO-C$_1$—C$_{20}$-alkyl, either of which is unsubstituted or substituted by at least one of C$_6$-aryl, C$_{10}$-aryl, C$_{12}$-aryl, halogen, amino, C$_1$—C$_6$-alkylamino, di-C$_1$—C$_6$-alkylamino, OH, C$_1$C$_6$-alkoxy, O-CO-C$_1$—C$_6$-alkyl or NH-CO-C$_1$—C$_6$-alkyl; a cycloalkyl or cycloalkenyl radical of 3 to 7 carbon atoms, or a cycloalkyl or cycloalkenyl radical of 3 to 7 carbon atoms substituted by alkyl with up to 8 carbon atoms; or an aryl or an aralkyl radical or an aryl or aralkyl radical substituted by nitro, lower alkyl, lower alkoxy or halogen, X represents Ch$_2$, O, S, NH or N-alkyl with up to 20 carbon atoms,
R$^2$ has the meaning of R$^1$, and can represent hydrogen when X denotes CH$_2$, the radicals R$^3$ independently of one another represent hydrogen, an acyl radical or alkyl radical with in each case up to 20 carbon atoms, a silyl radical and a phosphoric acid or phosphoric acid alkyl ester radical and
R$^4$ denotes hydrogen, methyl or —Ch$_2$—OR$^3$, with the proviso that one of the radicals R$^3$ always represents a phosphoric acid or phosphoric acid alkyl ester radical.

2. A compound according to claim 1, in which R$^1$ represents an alkyl radical or alkenyl radical with 10-20 carbon atoms.

3. A compound according to claim 1, in which the alkyl or acyl radical R$^3$ has 1-10 carbon atoms.

4. A compound according to claim 1, in which the phosphoric acid radical is a radical of the formula- PO(OH)$_2$, and the phosphoric acid alkyl ester radical is a radical of the formula

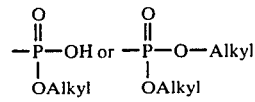

in which alkyl represents a straight-chain or branched alkyl radical with 1-20 carbon atoms.

5. A compound according to claim 4, in which the alkyl radical of the phosphoric acid ester radical has 1-5 carbon atoms.

6. A compound according to claim 1, wherein the compound is N-(glucopyranosyl-6phosphate)-N-octadecyl dodecanoic acid amide.

7. A compound according to claim 1, wherein the compound is N-(D-galactopyranosyl-6phosphate)-N-dodecyl-octadecanoic acid amide.

8. A compound according to claim 1, wherein the compound is N-octadecyl-N-(D-glucopyranosyl-6-phosphate)-decylurethane.

9. A compound according to claim 1, wherein the compound is N-(dodecyl)-N-(D-galactopyranosyl-6-phosphate)-tetradecanoic acid amide.

10. A compound according to claim 1, wherein the compound is N-(octadecyl)-N-(D-galactopyranosyl-6-phosphate)-tetradecanoic acid amide.

11. A compound according to claim 1, wherein the compound is N-(tetradecyl)-N-(D-glucopyranosyl-6-phosphate)-octadecanoic acid amide.

12. An immunosystem stimulating composition comprising an immunosystem stimulating effective amount of a compound according to claim 1 and a diluent.

13. A unit dose of a composition according to claim 1 in the form of a tablet, capsule or ampule.

14. A method of stimulating a patient's immune system comprising administering to such patient an amount effective therefor of a compound according to claim 1.

15. The method according to claim 14, wherein such compound is

N-(glucopyranosyl-6-phosphate)-N-octadecyl dodecanoic acid amide,

N-(D-galactopyranosyl-6-phosphate)-N-dodecyloctadecanoic acid amide,

N-octadecyl-N-(D-glucopyranosyl-6-phosphate)-decylurethane,

N-(dodecyl)-N-(D-galactopyranosyl-6-phosphate)-tetradecanoic acid amide,

N-(octadecyl)-N-(D-galactopyranosyl-6-phosphate)-tetradecanoic acid amide or

N-(tetradecyl)-N-(D-glucopyranosyl-6-phosphate)-octadecanoic acid amide.

* * * * *